United States Patent [19]

Dannels et al.

[11] 3,992,289

[45] Nov. 16, 1976

[54] METHOD FOR PRODUCTION OF SULFHYDRYL COMPOUNDS USING ULTRA-VIOLET RADIATION

[75] Inventors: Bobby F. Dannels; Emil J. Geering, both of Grand Island, N.Y.

[73] Assignee: Hooker Chemicals & Plastics Corporation, Niagara Falls, N.Y.

[22] Filed: Dec. 23, 1974

[21] Appl. No.: 535,631

[52] U.S. Cl. .................. 204/158 R; 204/159.18; 204/162 R; 260/42.37; 260/79; 260/830 S
[51] Int. Cl.² .......................................... B01J 1/10
[58] Field of Search ........ 204/159.18, 158 R, 162 R

[56] References Cited
UNITED STATES PATENTS

| | | | |
|---|---|---|---|
| 2,398,481 | 4/1946 | Vaughan et al. | 204/163 |
| 2,411,983 | 12/1946 | Vaughan et al. | 204/163 |
| 2,873,239 | 2/1959 | Nummy et al. | 204/158 |
| 3,398,200 | 8/1968 | Griesbaum et al. | 260/609 |
| 3,412,001 | 11/1968 | Edwards | 204/162 |
| 3,488,270 | 1/1970 | Griesbaum et al. | 204/162 |

*Primary Examiner*—Richard B. Turer
*Attorney, Agent, or Firm*—Peter F. Casella; James F. Mudd; David A. Stein

[57] ABSTRACT

An improved process is disclosed for production of sulfhydryl-terminated compounds by reaction of an allene and hydrogen sulfide initiated with ultraviolet light of wavelength above about 2600 Angstroms to obtain a colorless product of improved purity. The invention also includes the polymerization of an unsaturated hydrocarbon with the sulfhydryl-terminated product to prepare a sulfhydryl-terminated polythioether. These compounds are useful as chemical intermediates and precursors of elastomeric sealants, such as architectural sealants.

9 Claims, No Drawings

METHOD FOR PRODUCTION OF SULFHYDRYL COMPOUNDS USING ULTRA-VIOLET RADIATION

BACKGROUND OF THE INVENTION

1. Field of the Invention

The invention relates to improvements in the manufacture of sulfhydryl-terminated compounds useful as chemical intermediates and precursors of polythioether elastomeric sealants. By the method of the invention, products of improved purity are obtained by the addition of hydrogen sulfide to an allene compound. Subsequent addition of the sulfhydryl compound to a polyunsaturated olefin and/or an acetylene produces sulfhydryl-terminated polythioethers of improved purity and color. Such polythioethers are useful as a base polymer for sealants.

2. Description of the Prior Art

The ultraviolet light initiated free radical addition of hydrogen sulfide to allene in the liquid phase is known to produce sulfhydryl-terminated compounds such as mercaptans and sulfhydryl-terminated thioethers. U.S. Pat. No. 3,488,270 to Griesbaum et al. discloses the liquid phase addition of hydrogen sulfide to allene initiated with ultraviolet light. The reaction is conducted in quartz which transmits high energy ultraviolet light, i.e. ultraviolet light of wave length below 2600 Angstroms as well as low energy, long wavelength ultraviolet light, i.e. ultraviolet light of wavelength above about 2600 Angstroms. The reaction product is yellow and is usually contaminated with elemental sulfur. The formation of sulfur is accompanied by hydrogen evolution which may produce sufficient pressure to burst the reaction vessel. It has not been found feasible by conventional purification techniques to remove the discoloration. This disadvantage is particularly serious since the principal reaction product, 1,3-propane dithiol, is the precursor of sulfhydryl-terminated polythioethers which cure to valuable elastomeric sealants. Thus when the discolored dithiol, is reacted with an acetylenically and/or polyethylenically unsaturated compound in the presence of ultraviolet light as initiator according to known techniques (see U.S. Pat. Nos. 3,592,798 and 3,717,618 to Oswald and coassigned U.S. Ser. No. 501,716, filed Aug. 29, 1974, entitled "Polythioether Sealant Compositions" to B. F. Dannels), the sulfhydryl polythioether obtained is also discolored and of unsatisfactory curing characteristics and, hence is commercially unacceptable.

U.S. Pat. Nos. 2,398,481 and 2,411,983 to W. E. Vaughan et al. and U.S. Pat. No. 2,873,239 to W. R. Nummy et al. disclose the liquid phase addition of hydrogen sulfide to unsaturates initiated by ultraviolet light of wavelength above 2900-3000 Angstroms. The references neither relate to use of reactants having the distinctive allene unsaturated group, i.e. two carbon to carbon double bonds attached to the same carbon atom, nor teaches substantial conversion to sulfhydryl-terminated products in absence of a photosensitizing reagent.

U.S. Pat. No. 3,412,001 to J. R. Edwards discloses liquid phase reaction of hydrogen sulfide and olefins in the presence of ultraviolet light filtered through Pyrex, i.e. ultraviolet light of wavelength substantially above about 2800-2900 Angstroms. However, the patent does not relate to reaction of olefins containing the distinctive allene linkage and, moreover, requires limiting the reaction to conversion of no more than 22% of olefin starting material.

SUMMARY OF THE INVENTION

The invention relates to a novel improvement in the preparation of sulfhydryl-terminated compound by reaction of an allene compound with hydrogen sulfide which improvement comprises carrying out the reaction in the presence of ultraviolet light of wavelength substantially above about 2600 Angstroms to obtain a product substantially free of color and elemental sulfur.

The allene compound employed is either allene or a substituted allene. When allene is used, the principal sulfhydryl-terminated product is 1,3-propanedithiol. When a substituted allene is employed, the principal product is generally the corresponding substituted 1,3-propanedithiol and/or substituted 1,2-propanedithiol.

In a preferred embodiment of the invention the colorless sulfhydryl-terminated product is polymerized with an ethylenic or acetylenic compound to obtain a substantially colorless sulfhydryl-terminated thioether polymer curable to a polythioether sealant. The polymerization is also preferably carried out in the presence of ultraviolet light of wavelength substantially above 2600 Angstroms.

It was highly surprising to discover that ultraviolet light devoid of its high energy short wavelength bands would effectively initiate the reaction of the allene compound and hydrogen sulfide, avoid hydrogen evolution and provide a product devoid of undesirable color and elemental sulfur. The elimination of elemental sulfur and hydrogen formation in the reaction of the allene compound and hydrogen sulfide by the improved process of the invention is highly beneficial. The sulfur and hydrogen formation consumes hydrogen sulfide charged to the reaction and hydrogen evolution may produce dangerously high pressure in the reaction vessel.

DETAILED DESCRIPTION OF THE INVENTION AND PREFERRED EMBODIMENTS THEREOF

The reaction of the allene compound, i.e. allene or a substituted allene, and hydrogen sulfide is carried out substantially in accord with prior art reaction techniques except that the ultraviolet light incident on the reaction mixture is filtered to exclude ultraviolet light of short wavelength, i.e. wavelength of about 100 to about 2600 Angstroms. Generally ultraviolet light of the desired wavelength above 2600 Angstroms can be obtained by filtering broad spectrum ultraviolet light, i.e. of wavelength of 100-3800 Angstroms, through a vitreous material which is transparent to ultraviolet of the desired long wavelengths but opaque to ultraviolet light of wavelengths of 100-2600 Angstroms. Suitable vitreous materials for use in the invention include glasses such as the proprietary glass compositions manufactured by the Corning Glass Co., for example, Corex (No. 9700), Corex D, Chemical Pyrex (No. 7740), and Nonex (No. 7720) as well as lead glass and soda lime glass. Corex (No. 9700) which trasmits ultraviolet light of wavelengths above about 2600 Angstroms and Chemical Pyrex which transmits utraviolet light above about 2800 Angstroms are preferred filtering materials for obtaining ultraviolet light of the desired long wavelengths. The preferred materials contain 80–81% $SiO_2$, 13% $B_2O_3$, 4–5% $Na_2O$ and 2% $Al_2O_3$.

The ultraviolet transmission characteristics of various glasses (at 1 mm thickness) suitable for use in the invention are compared with those of glasses e.g. quartz and Vycor, which transmit undesirable short wavelength ultraviolet radiation in the section entitled "Transmission Characteristics of Quartz and Various Glasses" of "The General Electric Fused Quartz Catalog", Q-3, General Electric Co., 1952, the pertinent technology of which is incorporated herein by reference.

The reaction mixture obtained by reaction of the allene compound and hydrogen sulfide according to the invention is colorless and devoid of elemental sulfur. Generally only fractional distillation of the mixture, advantageously effected at diminished pressure, e.g., 0.1 to 100 mm, is required to provide a sulfhydryl-terminated product which reacts with a polyethylenically or acetylenically unsaturated compound to provide a substantially colorless sulfhydryl-terminated polythioether. This result is in unexpected contrast to that obtained by the prior art method utilizing ultraviolet light containing short wavelengths wherein the product, even after purification by distillation and absorption chromatography on alumnia, remains colored and produces, on reaction with the unsaturated compound, a yellow, unattractive, unacceptable polythioether.

The allene compound utilized in the present process is distinguished from ordinary olefins, such as ethylene, propylene and the like, in having two carbon-to-carbon double bonds attached to the same carbon atom. Allene compounds for use in general in the invention correspond to the general formula:

wherein $R_1$, $R_2$, $R_3$ and $R_4$ independently represent hydrogen and hydrocarbon radicals of 1 to 20 carbon atoms. The hydrocarbon radicals can be saturated straight-chain and branched chain alkyl radicals, cycloalkyl radicals, aryl radicals, aralkyl radicals and alkaryl radicals and $R_1$ and $R_3$, when alkyl, can be joined together to form a cycloaliphatic ring. The $R_1$, $R_2$, $R_3$ and $R_4$ radicals may be further substituted with conventional inert substituents such as halogen, e.g. chlorine, bromine and fluorine, carboalkoxy, i.e. ester substituents, carbonyl, i.e. keto, substituents and the like.

Typical allene reactants for use in general in the invention include the following:

Allene ($CH_2=C=CH_2$); 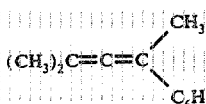 ; $(CH_3)_2C=C=C(CH_3)_2$;

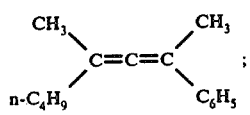 ;  ;  ;

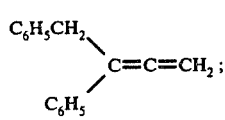 $C_6H_5CH=C=CHC_6H_5$; $CH_2=C=CHC_3H_7$; $CH_2=C=CHCH_3$;

$CH_2=C=CHC_{12}H_{25}$; $CH_2=C=C(CH_3)COC_6H_5$; 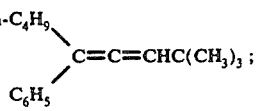

$(CH_3)_2C=C=CH_2$; $(C_6H_5)_2C=C=CHC(CH_3)_3$; $C_2H_5COCH=C=CH_2$;

 $CH_2=C=CHCH_2Cl$; 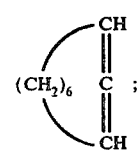 $C_5H_{11}CH=C=CH_2$

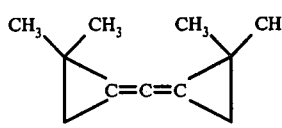 

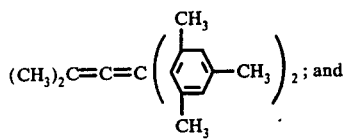 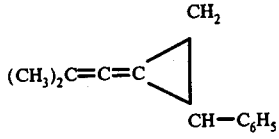

If desired, mixtures of these and equivalent allenes including homologs and isomers thereof can be charged as the allene compound reactant.

All of the foregoing representative compounds are known or are readily prepared by conventional synthetic techniques described in S. Patai, Ed. "The Chemistry of Alkenes," Interscience Publishers, 1964, pages 659–661, 762–3, 770, 1030–1060 and T. F. Rutledge, "Acetylenes and Allenes", Rheinhold Book Corporation, 1969, pages 4–31. The pertinent subject matter of these references is incorporated herein by reference.

Preferably the allene compound used is a lower aliphatic allene i.e. allene substituted with saturated alkyl groups of one to six carbon atoms or hydrogen. Preferably also an allene compound wherein the allene linkage is terminal, i.e. wherein $R_3$ and $R_4$ are hydrogen in the above formulas, is employed in the practice of the invention. Allene itself provides an especially good result. Frequently allene contains small amounts (up to about 0.5 to 10 mole percent) of methylacetylene which is also capable of reacting with hydrogen sulfide under the conditions of the present improved process. However, it is found that the presence of methylacetylene in the allene starting material in no way interferes with the beneficial excellent result obtained in the process. Accordingly such allene, can advantageously be used in the present process.

The reaction of hydrogen sulfide and the allene compound is carried out in the liquid phase i.e. under sufficient pressure to maintain the hydrogen sulfide and organic reactants and products in the liquid phase. In general the reaction may be effected at temperatures in the range of about −100° to about +95° C. at reaction pressures ranging from about atmospheric (0 p.s.i.g.) to about 3000 p.s.i.g. Preferable the reaction is carried out at about −70° to about +90° C, at pressures ranging from atmospheric to about 1300 p.s.i.g., especially at about −20° to about 70° C at pressures about 60 to about 400 p.s.i.g. If desired, the reaction can be carried out efficiently at low pressures ranging from about atmospheric pressure to about 60 p.s.i.g. at reaction temperatures of about −70° to −40° C.

The reaction of the hydrogen sulfide with the allene compound is exothermic. The temperature in the reaction vessel can be conveniently controlled by conventional cooling techniques. For example a cooling coil can be disposed within the reaction mixture or a cooling jacket can surround the reaction vessel. Also streams of air or nitrogen flowed along the outside walls of the vessel are useful in cooling the reaction vessel or for removing the heat generated by the ultraviolet light source.

The source of ultraviolet light employed in carrying out the present process include sunlight, a carbon arc, a mercury vapor lamp, a tungsten arc or Kronmeyer lamp. Advantageously the light source is disposed outside the reaction vessel which is constructed of the vitreous material employed in the invention to filter the ultraviolet light. Alternatively there is used a reaction vessel which is constructed predominantly of stainless steel, glass-lined stainless steel or other light-opaque material inert to the reactants and products of the present process but which contains a window or, advantageously a light well, constructed of the above described vitreous, ultraviolet filtering material.

If desired, a quartz well equipped with a removable filter insert of the desired vitreous material is used. When a reaction vessel containing a light well is employed the ultraviolet light source, advantageously a mercury vapor lamp, is disposed within the well during the reaction. As will be apparent to those skilled in the art, the reaction vessel used should be capable of withstanding superatmospheric pressure when such pressure is employed in carrying out the reaction.

The molar proportion of hydrogen sulfide to the allene compound employed can be from about 1:1 to about 20:1 and is preferably about 1.5:1 to about 15:1.

The moar ratio of hydrogen sulfide to the allene compound is an important feature of the process. This is so since the principal sulfhydryl-terminated product (i.e. 1,3-propanedithiol or substituted 1,3-propanedithiol is generally accompanied by a complex mixture of other sulfhydryl-terminated compounds including sulfhydryl-terminated thioethers and polythioethers with the yield of the desired dithiol being dependent upon the relative proportion of reactants charged. Typically the reaction of allene and hydrogen sulfide in preferred ratios produces a crude product mixture containing about 50 to 70% of the principal desired product, 1,3-propanedithiol, about 30 to 50% of sulfhydryl-terminated thioethers containing one, two, three, four or more thioether linkages (i.e. C-S-C) per molecule and about 0 to 5% of 1,2-propanedithiol. An especially good result is obtained in the present process employing hydrogen sulfide and the allene compound in a molar ratio of about 2.0:1 to 10:1.

The present improved addition of hydrogen sulfide to allene and substituted allene compounds is rapid with at least about 25% and usually about 70 to 100% conversion of the allene compound being achieved in about 1 to 15 hours. This result is unexpected in view of the low reaction rates and conversions obtained in the prior art condensation of allene and hydrogen sulfide as disclosed in the above-mentioned U.S. Pat. No. 3,488,270.

In carrying out the reaction of hydrogen sulfide and an allene compound according to the invention, a photosensitizing compound such as acetophenone, benzophenone and benzaldehyde may advantageously be charged to the reaction mixture in accord with the disclosure of U.S. patent application Ser. No. 535,632, filed Dec. 23, 1974 entitled "Improved sensitized Production of Sulfhydryl Compounds" to B. F. Dannels, filed of even date herewith, the pertinent technology of said application being incorporated herein by reference.

The reaction of hydrogen sulfide and allene compound can be carried out in an appropriate conventional inert solvent e.g. benzene, but is preferably effected in bulk to facilitate the recovering of the propanedithiol product. The desired propanedithiol suitable for condensation with an unsaturated hydrocarbon is readily recovered by a conventional purification technique, advantageously fractional distillation of the crude reaction mixture which is preferably carried out at reduced pressure, typically about 0.1 to 100 mm of mercury. Prior to distillation, the crude is advantageously stripped of volatiles, such as traces of allyl mercaptan and dissolved hydrogen sulfide by moderate heating, say at 90°–110° Centigrade, at diminished pressure, e.g. about 1 to 100 mm, for about 0.5 to 1.5 hours.

In a preferred embodiment of the invention the colorless 1,3-propanedithiol or substituted 1,3-propanedithiol is polymerized by reaction with an unsaturated organic compound to provide a substantially colorless high molecular weight sulfhydryl-terminated polythioether capable of being cured to an elastomer. The polymerization reaction proceeds by a free radical mechanism and can be initiated by conventional initiators such as cumene hydroperoxide, tertiary-butyl hydroperoxide, azo-bis-isobutyronitrile, azo-bis-2,4-dimethylvaleronitrile, gamma radiation and broad spectrum ultraviolet light, i.e. ultraviolet light of 100–3800 Angstroms wavelength. Preferably, however, the polymerization is initiated with ultraviolet light of wavelength substantially above about 2600 Angstroms, i.e. low energy ultraviolet light of the type employed in the above described reaction of the the allene compound and hydrogen sulfide.

The unsaturated compound which is reacted with the sulfhydryl-terminated product of the reaction of hydrogen sulfide and the allene is a hydrocarbon having at least one acetylene bond or at least two ethylenic bonds. Olefins with one ethylenic bond react but do not give polymeric products. Generally the acetylenically unsaturated reactant will contain 2 to 50 carbon atoms and can be of mono, di, tri or higher functionality, i.e. it can contain one, two, three or more unsaturated sites per molecule. The ethylenically unsaturated reactant will contain 3 to 50 carbon atoms and be of di, tri, or higher functionality. If desired a multifunctional unsaturated reactant containing both ethylenic and acetylenic unsaturation can be used. The unsaturated rectant may contain one or more halogen substituents, e.g. fluorine, chlorine, and bromine, attached either to a saturated or unsaturated carbon atom. Also the unsaturate may contain other inert substituents such as ether groups, aryl substituents such as phenyl, naphthyl and lower alkylphenyl, cycloalkyl substituents such as cyclopentyl, cyclohexyl and cyclododecyl and ester groups, i.e. carboxy-lower alkyl groups such as carboxymethyl. Cyclic, straight-chain and branched chain unsaturated compounds can be employed in the chain extension reaction.

Typical suitable unsaturated compounds for use in the invention include the following representative examples: allene and the above-indicated substituted allenes, cyclohexadiene-1,3, butadiene-1,3, pentadiene-1,3, pentadiene-1,4, hexadiene-1,5, hexadiene-1,4, 2-methylbutadiene-1,3, 2,4-dimethylhexadiene-2,4, acetylene, methyl acetylene, butyne-1, butyne-2, bis(-pentacosyl)acetylene, pentyne-2, hexyne-1, cetyne-1, octylacetylene, phenylacetylene, cyclopentadiene, 1,3,5-hexatriene, cyclopentylacetylene, 1,2-divinyl cyclohexane, 1,3,5-trivinylcyclohexane, 1,2, 4-trivinylcyclohexane, p-divinylbenzene, sym.-trivinylbenzene, unsaturated organic halides such as perfluorobutadiene-1,3, 2-chloromethylbutadiene-1,3, 2-bromomethyl pentadiene-1,3, perfluoro-propyne-1, and unsaturated ethers such as divinyl ether, diallyl ether, dimethallyl ether as well as the homologs and isomers of such compounds. Preferred unsaturated compounds contain up to 12 carbon atoms.

In order to obtain an elastomer of desirable mechanical properties for sealant applications the unsaturated reactant is preferably predominatly an acetylenically unsaturated compound, most preferably a monoacetylenically unsaturated compound and especially an aliphatic acetylene containing the unsaturation solely in the alpha or terminal positions. Use of a monofunctional aliphatic terminally unsaturated acetylene, e.g. methylacetylene, provides an especially good result. In order to provide desirable chain branching in the sulfhydryl-terminated polythioether product, the unsaturated reactant also advantageously contains a minor amount of a trifunctional unsaturated hydrocarbon, especially 1,2,4-trivinylcyclohexane.

The chain extension reaction can be carried out at temperatures of about −100° to +175°C, preferably about 0° to 70° C. at pressures ranging from about 1 to about 10 atmospheres, preferably from about 1 to 5 atmospheres. The reaction can be effected wholly in the liquid phase if desired, employing sufficient pressure to maintain the reaction constituents in the liquid state. However, when the unsaturated reactant is a gas at the particular reaction temperature used, it is advantageous to bubble or sparge the unsaturated reactant into the liquid reaction mass maintained at atmospheric pressure.

The molar ratio of unsaturated reactant(s) to sulfhydryl-terminated reactant charged to the polymerization reaction is generally about 0.7:1 to about 0.999:1. Molar ratios of unsaturated reactant to dithiol reactant of exactly 1:1 or greater can be used but are desirably avoided since such ratios provide polythioether products which terminate in unsaturated substituents rather than in sulfhydryl groups. Preferably the molar ratio of unsaturated compound(s) to sulfhydryl-terminated reactant is about 0.85 to about 0.99.

When, in accordance with an especially preferred embodiment of the invention, the unsaturated reactant contains a monofunctional acetylenic compound together with a small amount of tri-unsaturated compound, to effect desirable chain branching in the product, the proportion of trifunctional unsaturated compound charged is about 0.0005 to 0.05, preferably about 0.005 to 0.03 moles per mole of the sulfhydryl-terminated reactant, i.e. the dithiol.

The polymerization reaction is carried out in reaction equipment substantially similar to that employed in carrying out the reaction of hydrogen sulfide and the allene compound. When ultraviolet light of wavelength substantially above about 2600 Angstroms is used to initiate the polymerization according to a preferred mode of operation, the sulfhydryl-terminated polyethioether product is of substantially greater purity and higher molecular weight than the polythioether obtained in the comparable polymerization initiated with ultraviolet light containing the short wavelength, high energy ultraviolet radiation, i.e. ultraviolet light filtered through quartz or Vycor which contains ultraviolet light of wave lengths within the range of about 100 to about 2600 Angstroms. For example, preferred ultraviolet light initiation of the polymerization reaction results in a colorless sulfhydryl-terminated polythioether having a molecular weight of about 10,000 or greater after only a five hour reaction period, whereas the polymerization reaction initiated by ultraviolet light containing the short high energy wavelengths results in a polythioether of a molecular weight of only 1940 even though the reaction period is extended to ten hours. Furthermore, the latter reaction mixture is contaminated with an intractable gel which forms on the reaction vessel walls and is, in part, discolored. The foregoing result also indicates a rapidity of reaction when employing the preferred ultraviolet light initiation which is unexpected in view of the lower energy of the initiating ultraviolet light. Generally when initiated with the preferred wavelengths of ultraviolet light, the polymerization reaction mixture reaches its maximum viscosity (indicative of maximum product molecular weight) in only about 1 to 15 hours.

Advantageously, the polymerization reaction may be carried out in the presence of a photosensitizing compound such as is described above for the reaction of the allene compound and hydrogen sulfide.

The polymerization can be carried out in a conventional inert solvent or in an appropriate conventional water-surfactant emulsion system. Preferably the polymerization is conducted in bulk which permits direct recovery of the polythioether product without further purification steps. The sulfhydryl-terminated polythioether product is fluid and usually can be poured or decanted from the reaction vessel on completion of the reaction. Polymeric products of molecular weight of 20,000 or greater may be so viscous as to require extrusion from the reaction vessel.

The crude sulfhydryl-terminated polythioether is advantageously stripped of volatiles, e.g. low molecular weight cyclic polythioethers, which have an unpleasant odor, by heating the polymer product at about 170°–200° Centigrade under a diminished pressure of about 0.001 to 5 mm of mercury for about 0.5 to 5 hours. Alternatively, the low molecular weight cyclic polythioethers can be removed by conventional steam distillation.

The sulfhydryl-terminated polythioether which is recovered from the polymerization reaction of the invention is substantially colorless and, hence, of enhanced commercial value. This class of polythioether is important as reactive precursors, i.e. prepolymers, of architectural sealant elastomers, since they can be cross-linked to elastomeric three-dimensional networks using a variety of known curing techniques. Advantageously these sulfhydryl-terminated polythioethers can be cured by mixing about 1 to 20 grams per 100 grams of polythioether of an oxidizing agent such as lead dioxide, manganese dioxide, and calcium peroxide and allowing the mixture to cure at room temperature. Alternatively, the curing can be accomplished by mixing the sulfhydryl-polythioether with an epoxide compound containing at least two epoxy substituents per molecule and heating the resultant mixture until the desired three dimensional network is obtained. Also the sulfhydryl-terminated polythioethers can be cured by reaction with diepisulfides and the like.

In using the sulfhydryl-terminated polythioethers as sealants, various conventional adjuvants are normally added to the polythioether prior to initiation of the curing operation, for example stabilizers, plasticizers and various types of fillers. Typically carbon fillers such as carbon black, channel black, furnace or petroleum coke can be incorporated into the sulfhydryl in amounts up to about 200 parts filler per 100 parts by weight of polythioether. Mineral fillers can be used also including the usual non-carbon fillers of pigments such as titanium dioxide or the oxides, hydroxides, sulfides, carbonates, etc. of silicon, aluminum, magnesium, zinc, calcium, barium or the like, as well as the silicates or aluminates of the various metals indicated above. The production and curing of polythioether elastomeric sealant compositions from sulfhydryl-terminated polythioethers is more particularly described in aforementioned U.S. patent application Ser. No. 501,716, the pertinent technology of which is incorporated herein by reference.

The present sulfhydryl-terminated polythioethers are capable of in situ room temperature curing. Moreover, the resultant sealant compositions are resistant to degradation by oxygen, ozone and organic solvents. Accordingly such sealants are especially useful in architectural applications, for example for filling and sealing joints, and seams in many areas of construction including insulated glass windows, floors and pavements. A particular advantage of the present sulfhydryl-terminated polythioethers in such architectural sealant applications is their substantial lack of color. Thus, the present substantially colorless sulfhydryl-terminated polythioether products can be cured by a white or colorless curing agent, e.g. calcium peroxide, to provide an attractive seal devoid of discoloration.

In addition to the foregoing commercial applications, the elastomers and rubbers prepared by curing the sulfhydryl-terminated polythioethers can also be employed as printing rollers and gaskets.

The following examples serve to illustrate the various aspects of the invention but are not intended to limit it. Where not otherwise noted throughout this specification and claims, parts, percentages and proportions are by weight and temperatures are in degrees centigrade.

EXAMPLE 1

A 1.5 gallon stainless steel pressure vessel with a nickel head, and a 55 mm outside diameter quartz light well is equipped with pressure sensors, a thermocouple and a Chemical Pyrex (7740 Pyrex manufactured by the Corning Glass Co.) filter inserted in the light well. A 450 watt medium pressure mercury vapor arc (Hanovia Model 679A-36 ultraviolet lamp) is placed within the light well through which nitrogen gas coolant is circulated. The reaction vessel is cooled to about −20° in an aqueous ethylene glycol bath. Hydrogen sulfide and allene in a mole ratio of about 8.3:1 are charged to the vessel which is sealed.

The mercury vapor lamp is switched on and allowed to irradiate the reaction mass for about 14 hours during which the reaction pressure is about 180 to 235 psi. The reaction vessel is then vented to a receiver at atmospheric pressure to recover excess hydrogen sulfide and any unreacted allene. There is thus obtained 1790 grams, (corresponding to about 100% conversion based on allene) of clear colorless liquid product devoid of any suspended or precipitated solid. Vapor phase chromatographic analysis of the crude colorless reaction mixture indicates the presence of about 68.7 percent of propanedithiol (of which no more than 5 percent is 1,2-propanedithiol, the remainder being 1,3-propanedithiol) with the remaining portion of the crude reaction mixture being a mixture of sulfhydryl-terminated thioethers containing 1,2 or more thioether linkages per molecule. Traces of allyl mercaptan and dissolved hydrogen sulfide are removed from the reaction mixture by heating the latter at about 100° at 25 mm of mercury for about 1 hour. Fractional distillation of the crude reaction mixture through a packed column (16 inch length) provides a colorless fraction, b.p. 87–89/46 mm of mercury, amounting to about 50% of the distillation charge which is identified as 1,3-propanedithiol containing a trace of the corresponding 1,2-propanedithiol. The distillation residue is also colorless.

Substantially similar excellent clear colorless 1,3-propanedithiol can be obtained by replacing the Pyrex light well in the above reaction with one of Corex (9700 Corex manufactured by the Corning Glass Co.).

The composition of 7740 Pyrex glass is 81% $SiO_2$, 13% $B_2O_3$, 4% $Na_2O$, and 2% $Al_2O_3$.

The composition of 9700 Corex glass is 80% $SiO_2$, 13% $B_2O_3$, 5% $Na_2O$ and 2% $Al_2O_3$.

EXAMPLE 2

A 0.5 liter Vycor (7910 Vycor glass manufactured by Corning Glass Co.) round bottomed flask fitted with a stirrer, thermometer, gas inlet tube and dry ice reflux condenser is flushed with nitrogen. The flask is charged with 108 grams (about one mole) of distilled colorless 1,3-propanedithiol obtained by a procedure substantially similar to that of Example 1, and 4.1 grams (0.026 mole) of 1,2,4-trivinylcyclohexane. A 450 watt medium pressure mercury arc lamp of the type employed in Example 1 positioned horizontally 4 inches beneath the flask is allowed to illuminate the stirred reaction mixture for 30 minutes, then the reaction mass is saturated with gaseous methylacetylene charged through the gas inlet tube beneath the surface of the reaction mass which is maintained at a temperature of about 25°–30° at atmospheric pressure. The methylacetylene addition is continued at a rate sufficient to maintain slight reflux in the reaction mixture. After 10 hours, 34 grams (0.85 moles) of methylacetylene has reacted. The liquid sulfhydryl-terminated polythioether (146.3 grams) which is decanted from the reaction flask is heated at about 200° at a diminished pressure of about 0.5 mm of mercury for about 1 hour to remove volatiles of unpleasant odor. The product has a viscosity of 348 poises and a number average molecular weight of 1940 (vapor pressure osmometer in tetrahydrofuran).

The sulfhydryl polythioether product is colorless but cloudy and can be cured at room temperature to an attractive, substantially colorless polythioether elastomer with a suitable curing agent such as calcium peroxide in accord with the procedure of aforementioned U.S. patent application Ser. No. 501,716.

An intractable gelled material is found adhering to the walls of the reaction flask after removal of the sulfhydryl-terminated polythioether. While the gelled by-product is in the main colorless, that portion on the flask wall nearest the ultraviolet source has brown discoloration.

A substantially similar result is obtained when the above described polymerization reaction is carried out in a quartz flask, since quartz, like Vycor, is transparent to ultraviolet light of wavelength below about 2600 Angstroms.

EXAMPLE 3

The procedure of Example 2 is repeated substantially as described except that the ultraviolet lamp is positioned 2 inches from the flask which is of Chemical Pyrex rather than Vycor and 87 grams (0.81 mole) of the distilled colorless 1,3-propanedithiol and 3.18 grams (0.02 mole) of the 1,2,4-trivinylcyclohexane are charged. After about 5 hours reaction 30.8 grams (0.75 moles) of methylacetylene react and the recovered vacuum-stripped sulfhydryl-terminated polythioether is clear, colorless and very viscous (about 2000 poise viscosity or greater, indicative of a product molecular weight of 10,000 or greater). No gelled material is formed. The clear colorless sulfhydryl-terminated polythioether can be cured at room temperature to an attractive, substantially colorless polythioether elastomer by the procedure of Example 2.

Substantially similar excellent results are obtained when the pyrex reaction flask is replaced by one of Corex 9700, or ordinary soda lime glass.

Comparison of the results of Examples 2 and 3 indicate that the polymerization reaction is preferably initiated with ultraviolet light having a wavelength substantially above about 2600 Angstroms.

EXAMPLE 4

The procedure of Example 1 is repeated substantially as described except that the molar ratio of hydrogen sulfide to allene is 9.3:1. After a 9 hour reaction period there is obtained 1090 grams (corresponding to 71% conversion of allene) of clear colorless reaction mixture which contains about 66 mole percent of propanedithiol. Fractional distillation under diminished pressure of the reaction mixture provides a clear colorless 1,3-propanedithiol distillate and colorless distillation residue.

The distilled 1,3-propanedithiol product can be reacted with methylacetylene and 1,2,4-trivinylcyclohexane in accord with the procedure of Example 3 to obtain a commercially attractive colorless sulfhydryl-terminated polythioether curable to an attractive colorless polythioether elastomeric sealant.

EXAMPLE 5 (Control)

The procedure of Example 1 is repeated substantially as described except that the molar ratio of hydrogen sulfide to allene is about 8.7:1 and the Pyrex insert is omitted so that the quartz light well transmits to the reaction mixture ultraviolet light of wavelengths below about 2600 Angstroms as well as wave lengths of ultraviolet light up to about 3800 Angstroms. After an 11.2 hour reaction period, there is obtained 1213 grams (corresponding to a 72% conversion of allene) of crude reaction mixture which is yellow and cloudy indicating the presenc of suspended solid, which is identified as sulfur. Analysis of the reaction mass indicates the presence of about 58 mole percent of propanedithiol. Fractional distillation of the reaction mixture provides a 46% recovery (based on the distillation charge) of a 1,3-propanedithiol fraction, b.p. 84-87 at 39 mm of mercury, which is yellow but free of suspended sulfur. Neither refractionation nor absorption treatment, (on a vertical column filled with particulate absorbent alumnia) removes the yellow color of the distilled 1,3-propanedithiol.

The discolored, distilled 1,3-propanedithiol is reacted with methylacetylene and 1,2,4-trivinylcyclohexane substantially in accord with the procedure of Example 3. The resultant sulfhydryl polythioether is yellow and on being cured with a colorless curing agent provides an unattractive yellow polythioether elastomer.

A substantially similar undesirable result, i.e. a yellow propanedithiol product and formation of elemental sulfur, is also obtained when the above reaction of allene and hydrogen sulfide is carried out in a reactor equipped with a Vycor light well filter insert.

From comparison of the results of Examples 1 and 4 with that of control Example 5 it is apparent that initiation of the allene-hydrogen sulfide reaction with ultraviolet light of wavelength substantially above about 2600 Angstrom not only provides a dithiol and polymerization product devoid of color but also avoids formation of elemental sulfur.

EXAMPLE 6

The procedure of Example 3 is repeated substantially as described in polymerizing 114 grams (about 1.05 mole) of fractionally distilled 1,3-propanedithiol prepared as described in Example 1 with 0.86 grams (0.0053 mole) of 1,2,4 trivinylcyclohexane and 41.7 grams (1.04 mole) of methyl acetylene except that the polymerization is carried out in the presence of 0.53 grams (0.0044 mole) of acetophenone charged as a photosensitizing reagent and the ultraviolet light source is a 100 watt ultraviolet light positioned ½ inch beneath the pyrex flask. After a reaction period of about 5 hours there is obtained a liquid clear, substantially colorless sulfhydryl-terminated polythioether which, after being stripped of volatiles by heating at 200° for 1 hour at a diminished pressure of 0.05 mm of mercury, has a viscosity of about 20,000 poises and a molecular weight of about 16,800 (gel permeation chromatography). The sulfhydryl-terminated polythioether is cured to an excellent polythioether elastomer by a procedure substantially similar to that of Example 2. The foregoing procedure can be repeated to obtain sulfhydryl-terminated polythioethers of high molecular weight, e.g. of about 100,000 to 1,000,000 or higher.

It is to be understood that the invention is not limited to the specific examples which have been offered merely as illustrative and that modifications may be made without departing from the spirit of the invention.

What is claimed is:

1. In the liquid phase reaction of an allene compound with hydrogen sulfide to produce a sulfhydryl-terminated hydrocarbon, the improvement which comprises carrying out the reaction at a reaction termperature of about −100° to about 95° Centigrade, a reaction pressure of about 0 to about 3000 p.s.i.g. and a molar ratio of hydrogen sulfide to the allene compound of about 1:1 to about 20:1 in the presence of ultraviolet light of wavelength substantially above about 2600 Angstroms to obtain a sulfhydryl-terminated hydrocarbon substantially free of color and elemental sulfur.

2. The process of claim 1 wherein the allene compound is one wherein the allene linkage is terminal, the reaction temperature is about −70° to about 90° Centigrade, the reaction pressure is about 0 to 1300 p.s.i.g. and the molar ratio of hydrogen sulfide to the allene compound is about 1.5:1 to about 15:1.

3. The process of claim 2 wherein the allene compound is a lower aliphatic allene and the mole ratio of hydrogen sulfide to the allene compound is about 2:1 to about 10:1.

4. The process of claim 3 wherein the allene compound is allene.

5. The process of claim 4 wherein the ultraviolet light of wavelength substantially above about 2600 Angstroms is provided by passing ultraviolet light through vitreous material which is transparent to at least some wavelengths of light in the 2600–3800 Angstrom wavelength region but is substantially opaque to light in the 100–2600 wavelength region.

6. The process of claim 5 wherein the vitreous filter is Chemical Pyrex.

7. The process of claim 5 wherein the vitreous filter is Corex 9700.

8. In the liquid phase reaction of an allene compound with hydrogen sulfide to produce a sulfhydryl-terminated hydrocarbon the improvement of:
    1. carrying out the reaction of the allene compound and hydrogen sulfide at a reaction temperature of about −100° to about 95° Centigrade, a reaction pressure of about 0 to about 3000 p.s.i.g. and a molar ratio of hydrogen sulfide to the allene compound of about 1:1 to about 20:1 in the presence of ultraviolet light of wavelength above about 2600 Angstroms to obtain a product reaction mixture which is substantially free of color and elemental sulfur and
    2. recovering the sulfhydryl-terminated hydrocarbon, substantially free of color and elemental sulfur from said reaction mixture.

9. The product of the process of claim 8.

* * * * *